US 6,655,960 B2

(12) United States Patent
Fischer

(10) Patent No.: US 6,655,960 B2
(45) Date of Patent: Dec. 2, 2003

(54) TONGUE SUPPRESSING BITE BLOCK ADAPTABLE TO VARYING MOUTH AND TONGUE SIZES

(75) Inventor: Dan E. Fischer, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 10/002,822

(22) Filed: Nov. 1, 2001

(65) Prior Publication Data
US 2003/0082495 A1 May 1, 2003

(51) Int. Cl.⁷ .............................................. A61C 5/00
(52) U.S. Cl. ...................................................... 433/140
(58) Field of Search ........................... 433/140, 93, 94, 433/149, 136, 138; 600/237, 238, 240; 128/848, 859, 860, 861

(56) References Cited

U.S. PATENT DOCUMENTS

| | | | | |
|---|---|---|---|---|
| 20,905 A | * | 7/1858 | Thomas | 600/238 |
| 2,220,674 A | | 11/1940 | Bloomheart | 600/238 |
| 3,924,333 A | | 12/1975 | Erickson | 32/33 |
| 4,053,984 A | | 10/1977 | Moss | 32/33 |
| 4,167,814 A | | 9/1979 | Schubert | 32/33 |
| 5,340,313 A | | 8/1994 | Hussin | 433/136 |
| 5,588,836 A | | 12/1996 | Landis et al. | 433/93 |
| 5,590,643 A | | 1/1997 | Flam | 128/200.26 |
| 5,735,691 A | | 4/1998 | Fetter | 433/140 |
| 5,890,899 A | | 4/1999 | Sclafani | 433/140 |
| 6,244,866 B1 | | 6/2001 | Campbell | 433/140 |

OTHER PUBLICATIONS

PropEZ™ Plus, Silicone Mouth Props, advertisement, 1 Reality Ratings, vol. 15, Section 1, 2001, p. 478.

* cited by examiner

Primary Examiner—Kevin Shaver
Assistant Examiner—Melba Bumgarner
(74) Attorney, Agent, or Firm—Workman, Nydegger & Seeley

(57) ABSTRACT

A dental apparatus for maintaining the mouth of a patient in an open position during a dental procedure. The apparatus includes a bite block that is inserted into the patient's mouth between the upper and lower teeth on either side of a patient's mouth. Disposed in operable relation to the bite block is a tongue suppressor for confinement of the patient's tongue within a desired location, such as the bottom cavity, of the patient's mouth. The tongue suppressor includes a retention arm that extends across the tongue laterally away from the bite block. The bite block includes features, such as a plurality of slots or paired recesses, that allow for a portion of the tongue suppressor, such as the retention arm, retention prongs or an adjustment peg to be selectively inserted and retracted relative to the bite block to provide for lateral adjustment of the tongue suppressor relative to the bite block. In addition, the tongue suppressor can be moved vertically relative to the bite block to account for the tremendous variation between the sizes and shapes of different patient's mouths, teeth, tongues and the like.

21 Claims, 4 Drawing Sheets

TONGUE SUPPRESSING BITE BLOCK ADAPTABLE TO VARYING MOUTH AND TONGUE SIZES

BACKGROUND OF THE INVENTION

1. Field of the Invention

The present invention relates to dental implements and, more particularly, to novel apparatus for maintaining the mouth of a patient in an open position while retaining the tongue in a desired location. More particularly, the present invention encompasses bite blocks with an adjustable tongue suppressor.

2. Relevant Technology

When a dentist performs a procedure, the patient's mouth must be held open to provide access to the patient's teeth. In simple, short procedures, such as an examination or teeth cleaning, the patient may be able to open his mouth wide and long enough for the dentist to perform the dental procedure. However, in longer and more complex procedures, the patient may tire from holding his or her mouth open or, in the alternative, be unable to hold his or her mouth open due to the pain of the dental procedure or numbness resulting from the anesthesia. In these types of procedures, dental mouth props may be used by a dentist in an effort to mechanically maintain the patient's mouth in the open position.

As appreciated by those skilled in the art, dental mouth props may function in a variety of ways. For example, some prior art dental mouth props incorporate a tubular frame inserted between the cheek and gum of a patient's mouth. Dental mouth props of this general nature generally mask the outer surface of the teeth, thereby making it difficult to view, drill, fill and/or perform other dental procedures on the teeth. Moreover, the dental mouth prop is usually positioned on both sides of the mouth, thus having the effect of obscuring the dentist's view and access from all angles within the patient's mouth.

Other dental mouth props have been developed by those skilled in the art which engage the teeth of a patent. These prior art dental mouth props are typically inserted between the upper and lower molars on one side of the mouth allowing a dentist to view and have working access to a larger area of the patient's mouth. However, these devices have no provisions for patient comfort and may cut and irritate the patient's mouth, gums and cheeks. Often these types of dental mouth prop devices are small and could be accidentally swallowed by a patient causing severe injury to the patient.

As appreciated by those skilled in the art, a patient's tongue may also interfere with a dental procedure by interfering with the dentist's visibility and by interrupting the limited available work space within the patient's mouth. Traditionally, dentists have used a variety of implements in an effort to suppress the tongue during a dental procedure. For example, dentists have used hand-held suppressors to hold the tongue in place. However, the use of hand-held tongue suppressors restricts the dentist to the use of only one hand or requires a dental assistant to hold the suppressor in place. Hand-held suppressors can therefore crowd the available working space within the mouth and prevent a clear view of the targeted work area.

In view of the foregoing, efforts have been made to integrate into a single device the ability to prop open the patient's mouth while suppressing the tongue. An example is U.S. Pat. No. 6,244,866 to Campbell, which issued Jun. 12, 2001. The Campbell device includes a bite block sized and configured to engage the patient's teeth in order to thereby maintain the mouth in the desired propped-open orientation and a tongue suppressor that extends laterally from the side of the bite block. The tongue suppressor is sized and configured so as to be slidably disposed within a corresponding slot within the bite block so as to provide lateral adjustment of the tongue suppressor relative to the bite block.

Whereas the Campbell device represents an improvement over previous dental mouth props and tongue suppressors, it is limited in the range of adjustability of the tongue suppressor relative to the bite block. In view of the tremendous variability in the size and shape of the patient's mouths, dental arches, teeth and tongues, the adjustability feature provided by the Campbell device may not adequately cover all such variations in an optimal manner. Accordingly, there exists a need for a bite block/tongue suppressor having greater adjustability so as to accommodate any and all differences in the size and shape of patient's mouths, dental arches, teeth and tongues.

Such adjustable tongue suppressing bite blocks that provide greater adjustability are disclosed and claimed herein.

SUMMARY OF THE INVENTION

The present invention comprises an adjustable dental apparatus for suppressing the tongue and maintaining the mouth of a patient in an open position. The dental apparatus comprises a bite block that is used to keep the patient's mouth in the open position and a tongue suppressor adjustably connected to the bite block. In this way, a single device can be used to simultaneously maintain the patient's mouth in an open position to facilitate access to the patient's teeth while also suppressing the tongue so as to keep it from inadvertently (or purposefully) obstructing access.

In one embodiment of the invention, the bite block includes one or more slots therethrough configured to receive therein a corresponding portion of the tongue depressor in an adjustable fashion. The one or more slots provide or allow for at least two modes of adjustment of the tongue suppressor relative to the bite block. The first mode of adjustment allows for lateral movement of the tongue suppressor relative to the bite block, thereby providing the ability to extend or retract the tongue suppressor in order to effectively adjust the length thereof. In this way, the position of the tongue suppressor can be adjusted in order to account for varying tongue widths among different people. This adjustment is particularly advantageous for those embodiments in which the tongue suppressor includes a flange or other overhanging feature that engages a side of the tongue distal to the bite block.

The second mode of adjustment allows for vertical movement of the tongue suppressor relative to the bite block, thereby providing the ability to raise or lower the tongue suppressor relative to the bite block and the patient's teeth. In this way, the position of the tongue suppressor can be adjusted upwardly or downwardly in order to account for varying tongue thicknesses among different people, tooth heights, or other variations that result in variability between the relative heights of the tongue and tooth surfaces within different people.

Other, optional modes of adjustment are also within the scope of the invention, including but not limited to, adjustments that allow for one or more angular movements of the tongue suppressor relative to the bite block (e.g., lateral, axial or both).

The bite block and tongue suppressor can be of any desired design and material so long as they provide the aforementioned first and second modes of adjustment. In general, the tongue suppressor includes a retention arm that extends from its engagement with the bite block across the top of the tongue. The retention arm is the primary feature of the tongue suppressor that holds the tongue and prevents it from obstructing access to the patient's teeth. The tongue suppressor may optionally include a flange or other projection at an end distal to the bite block that projects or curves downward into the inferior aspect of the oral cavity (e.g., the bottom cavity of the mouth). This flange or other projection can engage a side of the tongue opposite to the bite block in order to provide an additional tongue suppression feature in addition to the retention arm.

The retention arm may be configured to slide freely into and out of the slot. Alternatively, retention mechanisms such as a friction fit, a mechanical lock, notches and the like may be incorporated into the design of the bite block and/or the tongue suppressor to more securely hold the tongue suppressor in the slot of the bite block in a desired position.

The bite block may be configured with one or more shoulders that extend along the sides of the teeth. These shoulders serve to position the bite block on and around the teeth and to prevent lateral slippage. Where shoulders are present on both sides of the bite block around the inside and outside of the teeth the shoulders may be of varying heights. Because the interior shoulder may project into a target area of the dental procedure, it may advantageously be of lesser height than the exterior shoulder to thereby provide more clearance than the exterior shoulder. A lower profile interior shoulder may also be less likely to rub on the roof of the mouth and cause pain or discomfort to the patient.

Since the bite block will generally be held in place by the teeth of a patient, the bite block may advantageously include two different surfaces that engage the upper and lower teeth, respectively. The surfaces may be elastically or plastically distortable, thus allowing the teeth of the patient to slightly penetrate and deform the surface area. In this way, the surfaces provide gentle engagement of the teeth. The surfaces may include ridges, indentations, ribs, or other features that provide means for engaging the teeth and preventing slippage of the bite block relative to the teeth.

The bite block may advantageously be employed on either side of the mouth, e.g., by reversing its orientation relative to the person's teeth or by removing and reversing the tongue suppressor relative to the bite block. The bite block may be manufactured to include an angle that matches the desired angle of an open mouth. The angle of engagement may vary depending on the age and size of a patient as well as the size of the area needed for conducting the dental procedure. The dentist may be provided with varying sized bite blocks and/or tongue suppressors to account for varying mouth sizes and shapes.

The tongue suppressing bite block may be formed, if desired, with rounded edges and surfaces to prevent injury to the soft tissue. The exterior surface of the bite block may be curved, for example, to conform to the general shape of a patient's mouth. The tongue suppressing bite block may be formed from one or more materials selected for their low cost and/or disposability. In addition, the tongue suppressing bite block may be pre-sterilized and packaged. Moreover, the tongue suppressing bite block may be treated with a desired flavoring.

As appreciated in the dental arts, during a dental procedure, fluid may begin to build up from salivation, bleeding and irrigation. Accordingly, the flange section of the tongue suppressor may include an access notch where suction can be applied to eliminate fluids retained in the lower cavity of the patient's mouth.

An emergency extraction mechanism may be incorporated into the tongue suppressing bite block to reduce the risk of a patient swallowing the apparatus during a dental procedure. For example, an aperture may be cut or formed in the tongue suppressor or bite block and a tether, such as a length of floss or string, may be secured to the aperture to allow a dentist or assistant to remove the apparatus from a patient's mouth in case of emergency.

As appreciated, the internal region of the mouth is a relatively small area to perform a procedure and can become crowded inside and outside by the introduction or proximity of excess dental implements. Accordingly, the tongue suppressing bite blocks in accordance with the present invention may advantageously be configured to fit entirely within a patient's mouth, thereby preventing overcrowding of the work area.

For purposes of disclosing various structural, comfort, protective or features that may be incorporated within the tongue suppressing bite blocks of the present invention, U.S. Pat. No. 6,244,866 is incorporated herein by reference. However, to the extent that U.S. Pat. No. 6,244,866 contains teachings that are incompatible with the second mode of adjustment described above and herein, as well the optional modes of adjustment, the present disclosure does not incorporate such teachings of U.S. Pat. No. 6,244,866.

In view of the foregoing, the tongue suppressing bite block is capable of maintaining the mouth of a patient in an open position while retaining the patient's tongue in the lower region of the mouth to avoid obfuscating the limited available work area within the patient's mouth. This facilitates dental procedures by improving visibility in and around the work area within a patient's mouth. The bite block is adjustable to accommodate varying sized and shaped mouths, teeth, tongues and other features that change from person to person.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings, in which.

DETAILED DESCRIPTION OF THE PREFERRED EMBODIMENTS

In order to better illustrate the structural and functional features of the adjustable tongue suppressing bite block according to the invention, the following detailed description is presented. It should be understood that the components of the present invention, as generally described and illustrated in the figures herein, could be arranged and designed in a wide variety of different configurations. Thus, the following detailed description of the invention, and as illustrated in FIGS. 1–7, is not intended to limit the scope of the invention, but is merely representative of the presently preferred embodiments of the invention.

Figure 1:
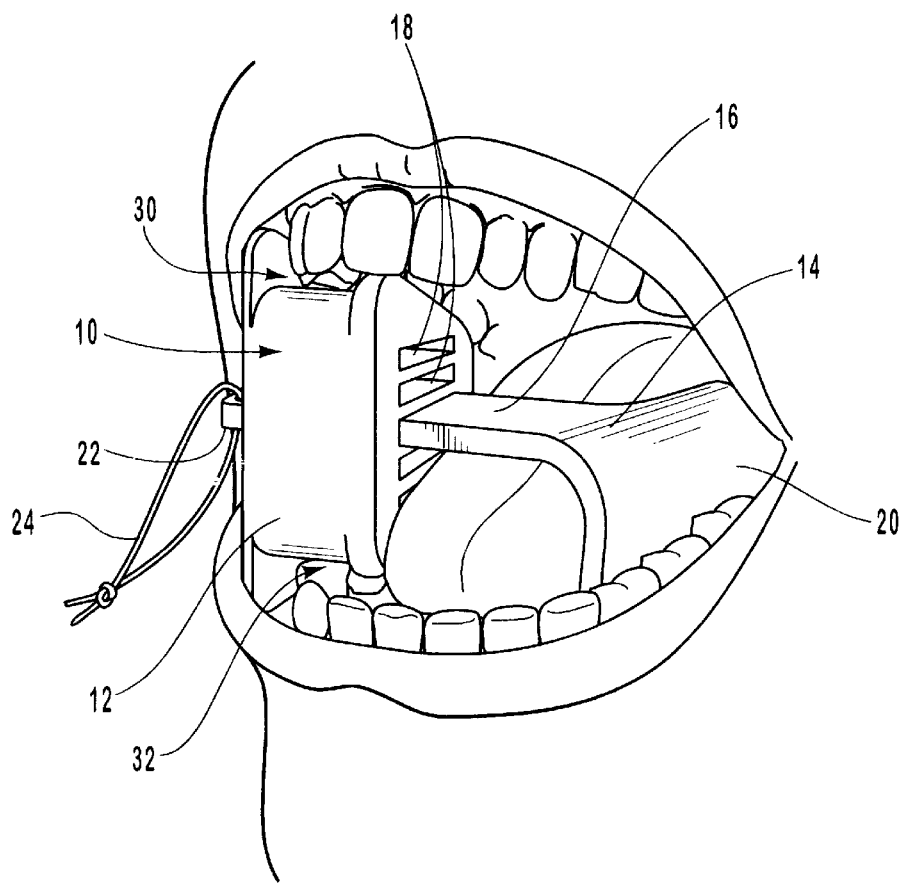
FIG. 1 is a perspective view of an embodiment of an adjustable tongue suppressing bite block that includes multiple slots in the bite block for vertical adjustment of the tongue suppressor and that is shown inserted within a patient's mouth.
Figure 2:
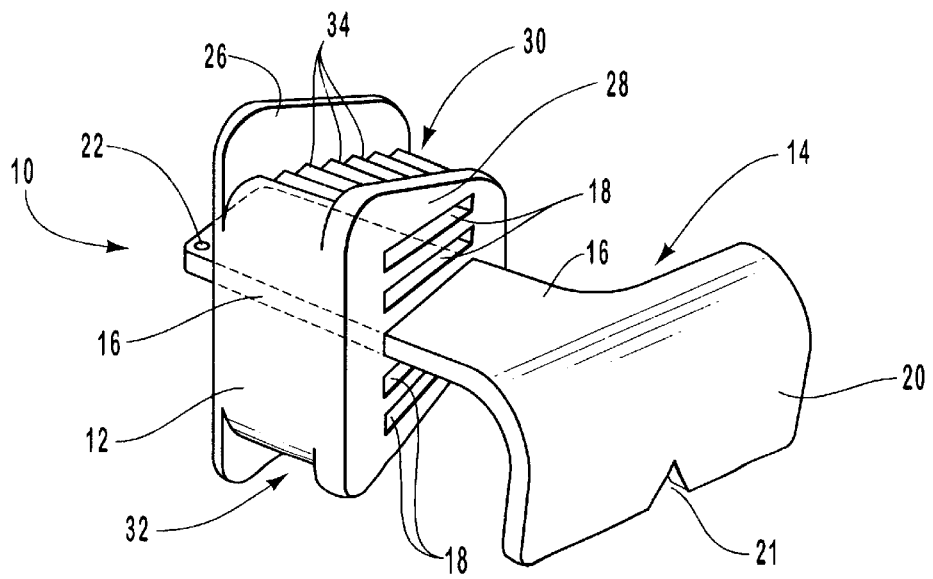
FIG. 2 is a perspective view of the embodiment illustrated in FIG. 1.
Figure 3:
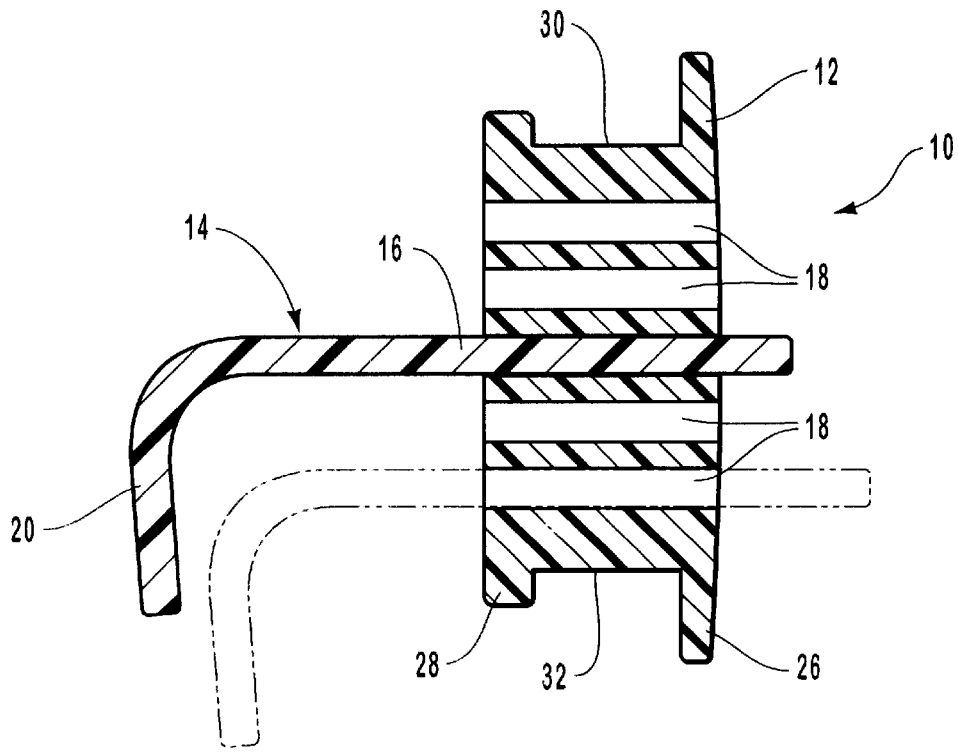
FIG. 3 is a cross-sectional view of the embodiment illustrated in FIGS. 1 and 2 depicting the vertical adjustability of the tongue suppressor relative to the bite block.

Reference is now made to FIGS. 1–3, which depict an embodiment of the invention that includes features for both lateral and vertical adjustability of the tongue suppression element. More particularly, these figures depict a tongue suppressing bite block system 10 that includes a bite block 12 and a tongue suppressor 14 connected or attached to the bite block 12 in an adjustable fashion, and adjustment means for selective lateral and vertical movement of a tongue suppressor relative to the bite block 12. The bite block is sized and configured for positioning in a person's mouth in order to maintain the person's mouth in an open position, while the tongue suppressor is oriented relative to the bite block so as to maintain the person's tongue within a confined region of the person's oral cavity when the bite block is positioned within the person's mouth.

The tongue suppressor 14 includes a retention arm 16 that is sized and configured so as to be slidably inserted into or retracted from within any one of a plurality of adjustment slots 18 within the bite block 12. This ability of the retention arm 16 to be selectively inserted or withdrawn from slots 18 provides two degrees of adjustability. First, selective insertion or retraction of the retention arm 16 relative to a single adjustment slot 18 results in the ability to lengthen or shorten the tongue suppressor 14 relative to the bite block 12. In this way, the tongue suppressing bite block 10 can account for, and be adjusted to accommodate, varying widths of tongues among different patients.

In addition, by withdrawing the retention arm 16 entirely from one adjustment slot 18 and then inserting it into another slot 18, the position of the tongue suppressor can be adjusted vertically relative to the bite block 12. In this way, the tongue suppressing bite block 10 can accommodate the great variability that exists between differently sized teeth, tongues, mouths, and the like among different patients. This function is a great improvement in the art, and it goes far beyond simply providing for lateral adjustability, as is the case where the bite block only includes a single slot for receipt of the retention arm.

The embodiment depicted in FIGS. 1–3 includes five adjustment slots 18. It will be appreciated, however, that any number of adjustment slots 18 may be included within the bite block 12 in order to provide the desired level of vertical adjustability. The only limitation to the number of slots is the size of the bite block 12 and the depth of the slots 18 and retention arm 16. Moreover, even though the adjustment slots 18 are depicted as being substantially parallel, it will be appreciated that the slots 18 can be angularly off-set one from another in order to provide different angular orientations, or pitches, of the tongue suppressor 14 relative to the bite block 12, thus providing greater adjustability and variability of the tongue suppressor 14 relative to the bite block 12. Accordingly, the interaction between the retention arm 16 and adjustment slots 18 comprises an example of the aforementioned adjustment means, as do any of the suggested variations.

The retention arm 16 of the tongue suppressor 14 may be sized and configured relative to the adjustment slots 18 so as to result in sufficient friction such that positive force is required to either advance or retract the retention arm 16 relative to the slots 18 of the bite block 12. In this way, the tongue suppressor 14 will tend to remain in a desired lateral orientation relative to the bite bock 12.

The tongue suppressor 14 further includes a flange or protruding portion 20 that curves or otherwise angles around the side of the patient's tongue in order to maintain the tongue at a desired spaced-apart relationship relative to the adjacent teeth (i.e., those teeth opposite the bite block 12). The interface between the flange 20 and the retention arm 16 is preferably curved for comfort and to better conform to the generally curved shape of the side of the tongue. The flange 20 ensures less obstructed access by the dentist or practitioner to the patient's teeth adjacent to the flange 20. In general, the retention arm 16 and flange 20 work together to maintain the tongue in a desired suppressed orientation within the mouth in a comfortable manner. Nevertheless, it will be appreciated that the tongue suppressor 14 need not include the flange 20 but may merely comprise the retention arm 16 in order to generally suppress the tongue at the bottom of the oral cavity.

As depicted in FIGS. 1–3, the flange 20 may extend rearwardly beyond the width of the retention arm 16 in order to provide tongue suppression further back within the patient's mouth so as to maintain the tongue away from the patient's molars. Although the retention arm 16 is depicted as having a single width so as to be fully insertable into one of the adjustment slots 18, it will be appreciated that the retention arm 16 may have varying widths with one width, for example, sized so as to fit within one of the adjustment slots 18, and another width (not shown) sized so as to provide a desired tongue suppression function independent of the function of insertion or retraction of the retention arm 16 into the slots 18 of the bite block 12.

In order to further assist the dentist or other practitioner in carrying out a desired dental procedure, the flange 20 may include an aspiration notch 21 in order to facilitate aspiration and removal of excess saliva, other liquids or debris from within the oral cavity, which tend to build up when the patient's mouth is open and the patient is unable to swallow or expel fluid from the oral cavity.

In order to provide additional safety, the tongue suppressing bite block 10 system may include means for attaching a leash or other safety feature if retrieval of the bite block from deep within the patient's mouth becomes necessary. For example, a leash hole 22 may be provided within the retention arm 16 for attachment of a leash 24 thereto.

As illustrated in FIGS. 1–3, the tongue suppressing bite block 10 is advantageously tapered from front to back in order to match the angle of an opened mouth. It will be appreciated that the angle may be varied from one device to another depending on the size of the patient's mouth and the degree of opening or closure that is desired. For example, if the dentist desires a larger work area or access to the teeth in the rear of the patient's mouth, the angle of the bite block 12 may be steeper in order to force the patient's mouth in a more open configuration. Conversely, the angle of the bite block 12 may be less, and the bite block 12 narrower, in the even that it is desired to work on the front teeth and where greater patient comfort is desired.

In order to maintain the bite block 12 in a desired position relative to one side of the patient's teeth, the bite block 12 may include an outer shoulder 26 and an inner shoulder 28 that extend from beyond an upper surface 30 and a lower surface 32 of the bite block 12 in order to effectively form a recess into which the teeth may be inserted during use. In this way, the outer shoulder 26 and inner shoulder 28 serve to prevent lateral movement of the bite block 12 relative to the patient's teeth in addition to whatever retention forces may be provided by the patient when simply biting down onto the bite block 12 in manner so that the patient's upper teeth engage the upper surface 30 and the lower teeth engage the lower surface 32 of the bite block 12.

In order to provide additional retention, the upper and lower surfaces 30, 32 may include ridges 34 that provide additional gripping ability or mechanical interaction between the patient's teeth and the upper and lower surfaces 30, 32 of the bite block 12.

The outer and inner shoulders 26, 28 may be formed having different heights. For example, the height of the outer shoulder 26 may be greater than the height of the inner shoulder 28 in order to provide greater retention while maintaining patient comfort in view of the anatomy of the oral cavity surrounding the teeth.

Figure 4:
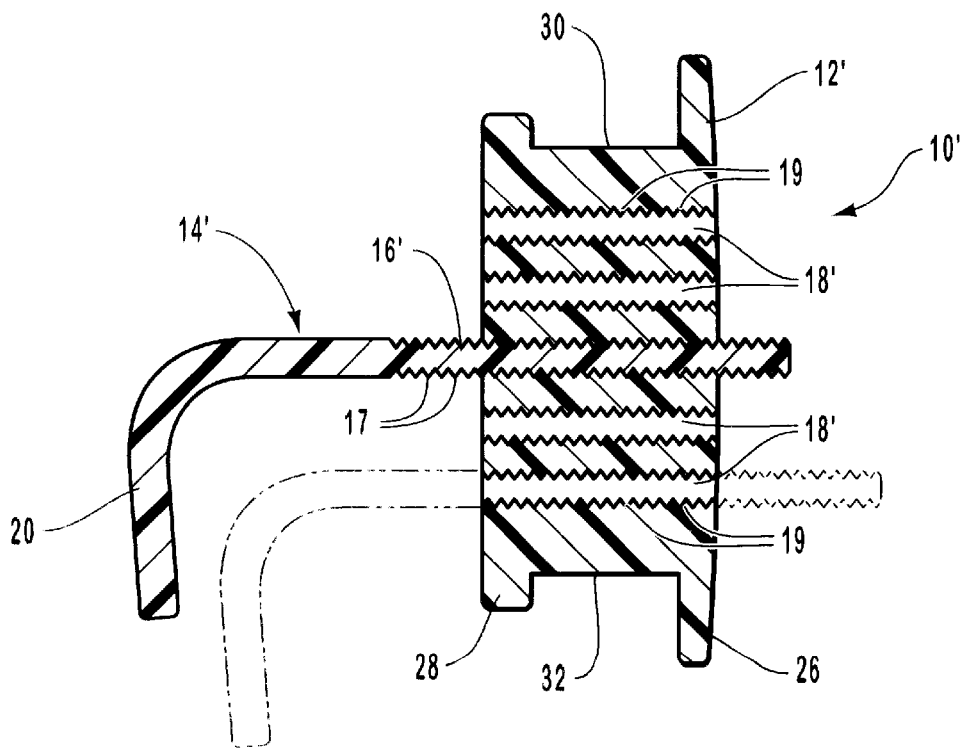
FIG. 4 is a cross-sectional view of an alternative embodiment of an adjustable tongue suppressing bite block that includes locking notches designed to partially restrict lateral movement of the tongue suppressor relative to the bite block.

FIG. 4 depicts an alternative embodiment of a tongue suppressing bite block system 10' that includes features for temporarily locking the tongue suppressor 14' within one of the adjustment slots 18' of the bite block 12'. In particular, the retention arm 16' of the tongue suppressor 14' includes a plurality of retention arm locking notches 17 that are sized and configured so as to engage corresponding slot locking notches 19 formed within the adjustment slots 18' of the bite block 12'. In this way, a force great enough to dislodge the arm locking notches 17 from within the slot locking notches 19 must generally be applied to insert or retract the retention arm 16' relative to one of the adjustment slots 18'. In most other respects, the tongue suppressing bite block system 10' of FIG. 4 is substantially similar to the tongue suppressing bite block system 10 depicted in FIGS. 1–3. The retention arm 16', adjustment slots 18', arm locking notches 17 and slot locking notches 19 comprise adjustment means according to the invention.

Figure 5:
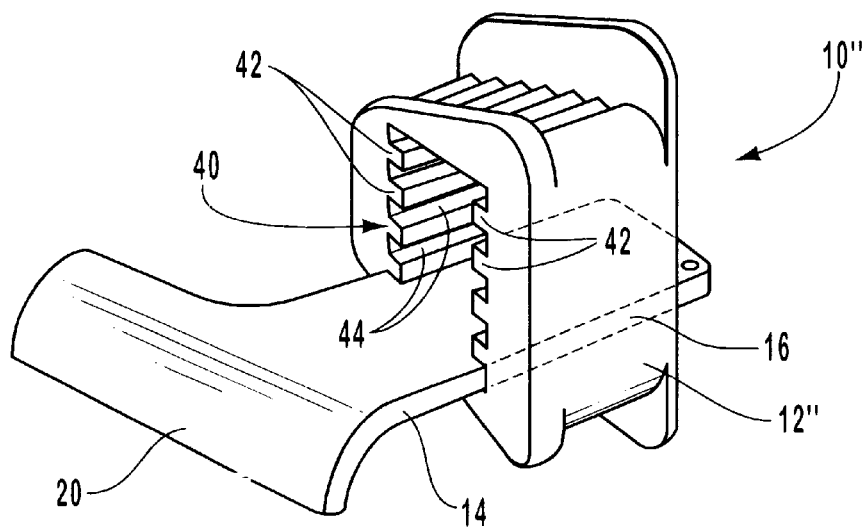
FIG. 5 is a perspective view of an alternative embodiment of a tongue suppressing bite block that includes a single opening and multiple ridges therein that provide both lateral and vertical adjustability of the tongue suppressor.

FIG. 5 depicts another embodiment of a tongue suppressing bite block system 10" that includes a bite block 12" and a tongue suppressor 14 substantially identical to the tongue suppressor 14 depicted in FIGS. 1–3. Instead of the plurality of adjustment slots 18 depicted in FIGS. 1–3, however, the bite block 12" in the embodiment of FIG. 5 includes a cavity 40 having a plurality of adjustment ridges 42 that define a plurality of adjustment recesses 44 into which the retention arm 16 may be selectively inserted. The adjustment ridges 42 and recesses 44 are sized and configured so as to define what are essentially a plurality of adjustment slots that are akin to the adjustment slots 18 depicted in FIGS. 1–3. The retention arm 16, cavity 40, adjustment ridges 42, and adjustment recesses 44 comprise adjustment means for selective vertical and lateral movement of a tongue suppression relative to a bite block.

The main difference between the embodiment depicted in FIG. 5 is that it requires less material to manufacture than the embodiment depicted in FIGS. 1–3, thereby decreasing the materials cost of the bite block 12" of the embodiment in FIG. 5 relative to the bite block 12 depicted in FIGS. 1–3. In most other respects, the tongue suppressing bite block system 10" of FIG. 5 functions in substantially the same manner as the embodiment of FIGS. 1–3.

Figure 6:
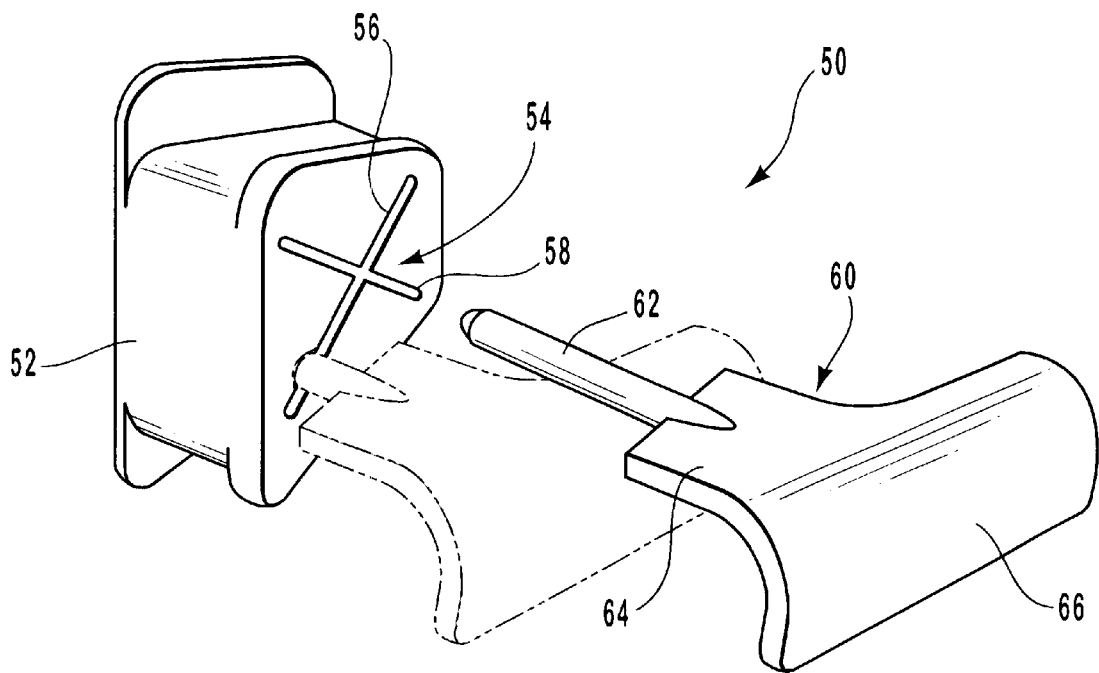
FIG. 6 is a perspective view of an alternative embodiment of a tongue suppressing bite block in which the tongue suppressor is adjustable upwardly, downwardly, forwardly.

FIG. 6 depicts yet another embodiment of a tongue suppressing bite block system 50 according to the invention configured for even greater adjustability. More particularly, the tongue suppressing bite block system 50 comprises a bite block 52 that includes a crisscrossing slot system 54 that provides greater degrees of adjustability of the tongue suppressing means relative to other embodiments. The slot system 54 includes a first compression slot 56 extending from the front lower end of the bite block 52 and extending to the rear upper end and a second compression slot 58 extending from the front upper end to the rear lower end of the bite block 52.

A tongue suppressor 60 is provided that includes an insertion peg 62 sized and configured so as to be inserted into one of the compression slots 56, 58 of the slot system 54. The insertion peg 62 is advantageously of greater diameter than the widths of the first and second compression slots 56, 58, and the bite block 52 comprises a resilient and flexible material, at least in the region of the slot system 54, in order for the compression slots 56, 58 to flex open so as to receive therein the insertion peg 62. The resiliency of the bite block 52 in the region of the slot system 54 causes the compression slots 56, 58 to exert sufficient gripping and/or frictional forces onto the insertion peg 62 so as to retain the tongue suppressor 60 in a desired vertical, angular, horizontal, and lateral orientation relative to the bite block 52. The bite block 52 is sufficiently flexible, however, in the region of the slot system 54 so as to allow for movement of the insertion peg 62 within the slot system 54 by exerting enough force on to the tongue suppressor 60 to overcome the retention forces exerted onto the insertion peg 62 by one or more compression slots 56, 58. This allows adjustment of the position of the tongue suppressor 60 relative to the bite block 52 so as to assume one of a large variety of varying vertical, horizontal, angular and lateral orientations relative to the bite block 52. The slot system 54 and insertion peg 62 comprise adjustment means for selective lateral and vertical adjustment of a tongue suppressor relative to a bite block. In addition, they comprise means for selective angular and horizontal movement of a tongue suppression relative to a bite block.

The tongue suppressor 60 further includes a retention arm 64 configured so as to extend over the surface of the patient's tongue in order to maintain the tongue in a suppressed orientation beneath the tongue suppressor 60 in the bottom of the patient's mouth. In addition, the tongue suppressor 60 may include a flange or other protrusion 66 extending from the retention arm 64 distal to the insertion peg 62 in order to provide an additional tongue suppression feature. The interface between the retention arm 64 and 66 may be curved so as to conform to the curvature of the patient's tongue between the top and side of the tongue so as to provide maximum comfort.

Figure 7:
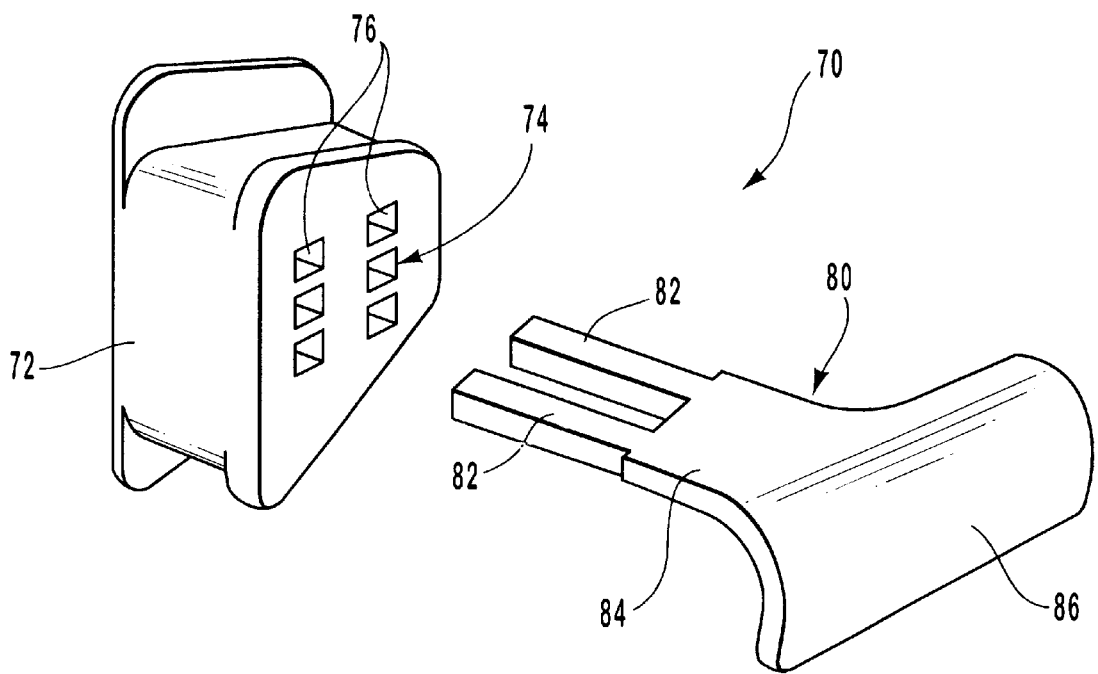
FIG. 7 is a perspective view of an alternative embodiment of a tongue suppressing bite block in which the tongue suppressor includes prongs designed to engage corresponding recesses within the bite block. backwardly relative to the bite block.

FIG. 7 depicts another embodiment of a tongue suppressing bite block system 70 according to the invention. The tongue suppressing bite block system 70 comprises a bite block 72, which includes a plurality of adjustment recesses 74 comprising individual pairs or sets of recesses 76, and a tongue suppressor 80. The tongue depressor 80 includes a retention arm 84 and a pair or set of adjustment prongs 82 that are sized and configured to be selectively received within desired one of the pairs or sets of adjustment recesses 76 within the bite block 72. The tongue suppressor 80 further includes a flange 86 that functions as described elsewhere in the specification. The adjustment prongs 82 and adjustment recesses 74 comprise adjustment means for selective lateral and vertical adjustment of a tongue suppressor relative to a bite block.

In general, the components of the tongue suppressing bite block according to the invention may be formed from resilient and flexible materials such as rubber, latex and other elastomeric materials. Various polymers may be selected for accommodation of stiffness and flexibility as may be structurally required. All or part of the tongue suppressing bite blocks according to the invention may be made from harder and more rigid materials such as thermoset materials, thermoplastic materials, foams and other plastics or composite materials, wood, metal, ceramics, fiberglass and the like. The components of the tongue suppressing bite blocks may be formed using various techniques, such as injection molding, blow molding, tumble molding, casting, vacuum forming, machining and the like.

The tongue suppressing bite block according to the invention may comprise higher quality materials that are durable and autoclavable (or otherwise sterilizable) in order to provide a device that can be reused a number of times. In the alternative, the tongue suppressing bite blocks may be formed from inexpensive materials that allow them to be disposable and intended only for a single use. Disposability eliminates risks associated with improper sterilization between uses. In either case, the tongue suppressing bite blocks of the invention may be advantageously sterilized at the point of manufacture and packaged in a sterile manner so as to maintain sterility until opened for use.

In order to mask the unpleasant taste that may be detected when using certain materials in the manufacture of the tongue suppressing bite blocks, the apparatus may be coated or infused with one or more flavoring agents so as to provide a more pleasant taste. Examples include bubble gum, mint, grape, cherry, chocolate and the like in order to increase the palatibilty of the device when inserted into the patient's mouth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An adjustable tongue suppressing bite block system, comprising:
    a bite block sized and configured for positioning in a person's mouth in order to maintain the person's mouth in an open position, said bite block having upper and lower surfaces for engagement with a person's upper and lower teeth when positioned within the person's mouth;
    a tongue suppressor adjustably attached to said bite block and oriented so as maintain the person's tongue within a confined region of the person's oral cavity when said bite block is positioned within the person's mouth; and
    adjustment means for selective lateral and vertical movement of said tongue suppressor relative to said bite block, said adjustment means comprising:
        at least one of a plurality of adjustment slots or adjustment recesses within said bite block; and
        at least one of a retention arm, adjustment prongs or an insertion peg within said tongue suppressor.

2. An adjustable tongue suppressing bite block system as defined in claim 1, wherein said bite block includes a plurality of slots, each of which is sized and configured to selectively receive therein a portion of said tongue suppressor in a manner so as to provide said selective lateral and vertical movement of said tongue suppressor relative to said bite block.

3. An adjustable tongue suppressing bite block system as defined in claim 2, wherein each of said plurality of slots is parallel to the other slots such that selectively removing said portion of said tongue depressor from one of said slots and inserting it into another of said slots results in vertical movement of said tongue depressor relative to said bite block.

4. An adjustable tongue suppressing bite block system as defined in claim 2, wherein said tongue suppressor is slidably connected to at least one of said slots in a manner so as to provide for selective lateral extension and retraction of said tongue suppressor relative to said bite block.

5. An adjustable tongue suppressing bite block system as defined in claim 2, wherein at least one of said slots and a portion of said tongue depressor includes locking notches for temporarily locking said tongue depressor is a desired orientation relative to said bite block.

6. An adjustable tongue suppressing bite block system as defined in claim 2, wherein two of said plurality of slots are oriented in a criss-cross fashion so as to allow for selective horizontal and angular movement of said tongue suppressor relative to said bite block in addition to said selective lateral and vertical movement.

7. An adjustable tongue suppressing bite block system as defined in claim 2, wherein at least a region within said bite block defining said plurality of slots comprises a resilient material.

8. An adjustable tongue suppressing bite block system as defined in claim 1, wherein said bite block comprises a cavity and a plurality of adjustment ridges that define a plurality of adjustment recesses into which a portion of said tongue suppressor can be selectively inserted and retracted in a manner so as to provide said selective lateral and vertical movement of said tongue suppressor relative to said bite block.

9. An adjustable tongue suppressing bite block system as defined in claim 1, wherein said bite block includes a plurality of adjustment recesses and wherein said tongue suppressor includes prongs that are sized and configured so as to be selectively inserted and retracted from said adjustment recesses in order to provide said selective lateral and vertical movement of said tongue suppressor relative to said bite block.

10. An adjustable tongue suppressing bite block system as defined in claim 1, wherein said upper and lower surfaces of said bite block comprise a plurality of ridges for enhanced retention of said bite block relative to the person's teeth when positioned within the person's mouth.

11. An adjustable tongue suppressing bite block system as defined in claim 1, wherein said bite block is angled in a manner so as to provide for a desired degree of opening or closure of the person's mouth, and wherein said upper and lower surfaces of said bite block comprise a resilient material.

12. An adjustable tongue suppressing bite block system as defined in claim 1, wherein said tongue suppressor includes a retention arm adjustably connected to said bite block and a flange extending downwardly from an end of said retention arm distal to said bite block.

13. An adjustable tongue suppressing bite block system, comprising:
- a bite block sized and configured for positioning in a person's mouth in order to maintain the person's mouth in an open position, said bite block having upper and lower surfaces for engagement with a person's upper and lower teeth when positioned within the person's mouth;
- a plurality of slots within said bite block;
- a tongue suppressor adjustably attached to said bite block and oriented so as maintain the person's tongue within a confined region of the person's oral cavity when said bite block is positioned within the person's mouth, at least a portion of said tongue suppressor being sized and configured for selective insertion into and retraction from said slots in a manner so as to provide selective lateral and vertical movement of said tongue suppressor relative to said bite block.

14. An adjustable tongue suppressing bite block system as defined in claim 13, wherein each of said plurality of slots is parallel to the other slots such that selectively removing said portion of said tongue depressor from one of said slots and inserting it into another of said slots results in vertical movement of said tongue depressor relative to said bite block.

15. An adjustable tongue suppressing bite block system as defined in claim 13, wherein said tongue suppressor is slidably connected to at least one of said slots in a manner so as to provide for selective lateral extension and retraction of said tongue suppressor relative to said bite block.

16. An adjustable tongue suppressing bite block system as defined in claim 13, wherein two of said plurality of slots are oriented in a criss-cross fashion so as to allow for selective horizontal and angular movement of said tongue suppressor relative to said bite block in addition to said selective lateral and vertical movement.

17. An adjustable tongue suppressing bite block system as defined in claim 13, wherein at least a region within said bite block defining said plurality of slots comprises a resilient material.

18. An adjustable tongue suppressing bite block system, comprising:
- a bite block sized and configured for positioning in a person's mouth in order to maintain the person's mouth in an open position, said bite block having upper and lower surfaces for engagement with a person's upper and lower teeth when positioned within the person's mouth;
- a tongue suppressor adjustably attached to said bite block and oriented so as maintain the person's tongue within a confined region of the person's oral cavity when said bite block is positioned within the person's mouth; and
- a plurality of adjustment recesses sized and configured so as to receive therein a portion of said tongue suppressor in a manner so as to provide selective lateral and vertical movement of said tongue suppressor relative to said bite block.

19. An adjustable tongue suppressing bite block system as defined in claim 18, wherein said tongue suppressor includes at least one of (i) a retention arm that is selectively received within two of said adjustment recesses or (ii) adjustment prongs that are selectively received with a set of said adjustment recesses.

20. An adjustable tongue suppressing bite block system, comprising:
- a bite block sized and configured for positioning in a person's mouth in order to maintain the person's mouth in an open position, said bite block having upper and lower surfaces for engagement with a person's upper and lower teeth when positioned within the person's mouth;
- a tongue suppressor adjustably attached to said bite block and oriented so as maintain the person's tongue within a confined region of the person's oral cavity when said bite block is positioned within the person's mouth; and
- a cavity and a plurality of adjustment ridges within said bite block that define a plurality of adjustment recesses into which a portion of said tongue suppressor can be selectively inserted and retracted in a manner so as to provide selective lateral and vertical movement of said tongue suppressor relative to said bite block.

21. An adjustable tongue suppressing bite block system, comprising:
- a bite block sized and configured for positioning in a person's mouth in order to maintain the person's mouth in an open position, said bite block having upper and lower surfaces for engagement with a person's upper and lower teeth when positioned within the person's mouth, said bite block including a plurality of adjustment recesses; and
- a tongue suppressor adjustably attached to said bite block and oriented so as maintain the person's tongue within a confined region of the person's oral cavity when said bite block is positioned within the person's mouth, said tongue suppressor including prongs that are sized and configured so as to be selectively inserted and retracted from said adjustment recesses in order to provide said selective lateral and vertical movement of said tongue suppressor relative to said bite block.

* * * * *

UNITED STATES PATENT AND TRADEMARK OFFICE
CERTIFICATE OF CORRECTION

PATENT NO.    : 6,655,960 B2
DATED         : December 2, 2003
INVENTOR(S)   : Dan E. Fischer It is certified that error appears in the above-identified patent and that said Letters Patent is hereby corrected as shown below:

Column 1,
Line 42, please replace "patent" with -- patient --

Column 5,
Line 13, after "and" please insert -- backwardly relative to the bite block; and --
Lines 17-18, after "bite block" remove "backwardly relative to the bite block; and"

Signed and Sealed this

Twenty-first Day of September, 2004

JON W. DUDAS
*Director of the United States Patent and Trademark Office*